(12) United States Patent
Suzuki et al.

(10) Patent No.: US 6,627,217 B1
(45) Date of Patent: Sep. 30, 2003

(54) EXTERNAL PREPARATION

(75) Inventors: Yasuyuki Suzuki, Tokyo (JP); Yoshiko Yoshino, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/869,246

(22) PCT Filed: Dec. 27, 1999

(86) PCT No.: PCT/JP99/07360

§ 371 (c)(1),
(2), (4) Date: Jun. 27, 2001

(87) PCT Pub. No.: WO00/38731

PCT Pub. Date: Jul. 6, 2000

(30) Foreign Application Priority Data

Dec. 28, 1998 (JP) .......................................... 10-372968

(51) Int. Cl.⁷ ........................ A61K 13/02; A61K 31/74; A61K 9/06

(52) U.S. Cl. ................. 424/443; 424/78.03; 424/78.05; 424/401; 514/772.3

(58) Field of Search ................................. 424/401, 443, 424/78.03, 78.05; 514/772.3

(56) References Cited

FOREIGN PATENT DOCUMENTS

| JP | 59-62518 | 4/1984 |
| JP | 8-113533 | 5/1996 |
| JP | 10-265409 | 10/1998 |
| WO | WO95/35093 | * 12/1995 |

* cited by examiner

*Primary Examiner*—Carlos A. Azpuru
(74) *Attorney, Agent, or Firm*—Sughrue Mion, PLLC

(57) ABSTRACT

The present invention is a preparation for external use which contains a basic drug, polyvinyl pyrrolidone and a carboxyvinyl polymer and which has a pH of 4 to 9.

The present invention has made it possible to provide a new preparation for external use which enables a drug to show a long-lasting action even at a damaged site of the skin.

10 Claims, No Drawings

EXTERNAL PREPARATION

TECHNICAL FIELD

The present invention relates to a preparation for external use containing a basic drug whose long-lasting action has been improved.

BACKGROUND ART

Dermal preparations for external use are excellent dosage forms permitting drugs to act directly on the sites of action and they find wide use.

As a general characteristic of preparations for external use, low absorption through the skin can be pointed out. Thus far, therefore, studies have been made of techniques for promoting drug absorption through the skin with the use of percutaneous absorption promoters. However, preparations for external use which use such percutaneous absorption promoters currently fail to obtain persistent effects.

As a method for allowing a drug to stay at the affected site to improve its long-lasting action, Japanese Patent Kokai Hei No. 10-265409 discloses a technique which involves adding fatty acid esters of aliphatic polyhydric alcohols, and certain types of polyhydric alcohols.

With regard to injections, on the other hand, WO95/35093 discloses a method for sustained release of a drug administered by injection and this technique comprises adding a polyacid and a water soluble nonionic polymer to the drug and gelling the mixture in a physiological environment to permit persistent drug release.

These techniques hitherto known in the field of techniques for prolonging the action of preparations for external use have been unsuccessful in showing a sufficiently long-lasting action on the skin damaged by wounds or inflammations, or at mucosal sites.

The present invention aims to provide a new technique which can achieve a long-lasting action of a drug even on a damaged skin or at a mucosal site.

DISCLOSURE OF THE INVENTION

The inventors of the present invention have conducted various studies to solve the problem. As a result, they found that when polyvinyl pyrrolidone and carboxyvinyl polymer were simultaneously used with a basic drug, and the mixture was adjusted to a specific pH, the mixture gave an excellent preparation for external use capable of showing a long-lasting action even when applied to a damaged skin or a mucosal site. This finding led them to accomplish the present invention.

That is, the present invention is a preparation for external use which contains a basic drug, polyvinyl pyrrolidone and carboxyvinyl polymer and which has a pH of 4 to 9.

The basic drug herein refers to a compound having a basic moiety in the structure, preferably, a compound having an amino group. Its examples include anti-inflammatories (bufexamac, indometacin, diclofenac, antipyrine, mefenamic acid, piroxicam, oxyphenbutazone, phenylbutazone, mepirizole, etc.), hair growers (minoxidil, etc.), vasoconstrictors (naphazoline, phenylephrine, etc.), antimycotics (croconazole, miconazole, econazole, clotrimazole, isoconazole, pyrrolnitrin, terbinafine, omoconazole, lanoconazole, liranaftate, itraconazole, fluconazole, tolnaftate, sulconazole, bifonazole, etc.), and local anesthetics (lidocaine, dibucaine, oxybuprocaine, etc.). Their salts are also usable.

The amount of the basic drug added differs according to its type of the drug, but is generally 0.1 to 5% by mass based on the entire mass of the preparation.

As the carboxyvinyl polymer used herein, those which are generally used as a base ingredient and the like in pharmaceuticals can be used. The use of a base ingredient such as hyaluronic acid instead of carboxyvinyl polymer does not offer a sufficient long-lasting action. Thus, carboxyvinyl polymer is an essential ingredient for exhibiting a long-lasting action in the preparation for external use. The amount of the carboxyvinyl polymer added is preferably 0.1 to 6 parts by mass per part by mass of the basic drug.

As the polyvinyl pyrrolidone used herein, those which are generally used as a base ingredient and the like in pharmaceuticals can be used. The amount of the polyvinyl pyrrolidone added is preferably 0.5 to 10 parts by mass per part by mass of the basic drug.

The preparation for external use according to the present invention may further contain polyethylene glycol and this is preferred because the long-lasting action of the drug on the affected site is further improved. The amount of the polyethylene glycol is preferably 10 to 50% by mass based on the entire mass of the preparation.

The preparation for external use according to the present invention needs to be in the pH range of 4 to 9, but a range of pH 4 to 8 is further preferred. A pH of less than 4 is not preferred in maintaining salability. A pH in excess of 9 may cause skin irritation.

For pH adjustment, use of a neutralizing agent which can be added into the preparation for external use, and an amine-based neutralizing agent is particularly preferred. Preferred examples of the neutralizing agent are triethanolamine, diethanolamine, triethylamine, diethylamine, isopropanolamine, diisopropanolamine, triisopropanolamine, di(2-ethylhexyl)amine, tetrahydroxypropylethylenediamine, and monoethanolamine.

Further addition of alcohols is preferred in terms of adhesion to the skin. No addition of alcohols may result in poor wetting of the skin with a liquid preparation, or poor adhesion of the liquid preparation to the skin, eventually leading to an insufficient pharmacological effect. As the alcohols to be added, common alcohols which can be used in preparations for external use are usable. Preferably, they include, for example, ethanol, isopropanol, propylene glycol, and 1,3-butylene glycol, and these alcohols can be used as mixtures. The amount of the alcohols added is preferably 10 to 70% by mass based on the entire mass of the preparation.

The concept of the preparation for external use as used herein includes preparations for cutaneous administration (liquids, creams, ointments, gels, patches, aerosols, etc.) and transmucosal preparations (nasal drops, oral preparations, suppositories, etc.), and can be in any of these common dosage forms. The present invention is particularly effective in the case of formulating liquid preparations for external use which have so far been defied the efforts to make them release the drug slowly.

The preparation for external use according to the present invention can contain ingredients which can be mixed into preparations for external use in qualitative and quantitative ranges not impairing the effects of the present invention and it can be produced by an ordinary method.

BEST MODE FOR CARRYING OUT THE INVENTION

Hereinafter, the present invention will be described in greater detail by the following Examples and Test Example.

EXAMPLES

Liquid preparations were obtained in the customary manner according to the formulations shown in Table 1 (W/V%; however, purified water was in mL).

TABLE 1

|  | Ex. 1 | Ex. 2 | Comp. Ex. 1 | Comp. Ex. 2 | Comp. Ex. 3 | Comp. Ex. 4 |
|---|---|---|---|---|---|---|
| Dibucaine hydrochloride | 1.0 | 1.0 | 1.0 | 1.0 | 1.0 | 1.0 |
| Carboxyvinyl polymer | 0.2 | 1.0 | — | — | — | — |
| Polyvinyl pyrrolidone K90 | 1.0 | 1.0 | — | 1.0 | — | — |
| Polyacrylic acid | — | — | — | — | 1.0 | — |
| Hyaluronic acid | — | — | — | — | — | 1.0 |
| Diisopropanolamine | 0.25 | 1.25 | — | — | 1.25 | — |
| Ethanol | 45 | 45 | 45 | 45 | 45 | 45 |
| Purified water | total 100 | total 100 | total 100 | total 100 | total 100 | total 100 |
| pH (diluted 20-fold) | 7.33 | 7.70 | 6.35 | 6.33 | 6.50 | 6.25 |

Test Example 1

Skin Permeation Test

A frozen skin of a Yucatan micropig (YMP) was thawed gradually at room temperature. Fat under the skin was removed and the skin was cut to a piece of 2.5 cm square. An adhesive tape was applied to the piece of skin and stripped off: this cycle was repeated 20 times to damage the piece of skin. Using a diffusion cell with an effective area of 0.95 cm$^2$, the test liquid preparation was passed through the piece of skin, and received into a receiver solution (3 ml of phosphate buffer; pH, 7.4) which was stirred at 37° C. At suitable time intervals, the receiver solution was sampled in an amount of 1 ml, and replenished with a fresh solution. This procedure was repeated. The concentration of the drug in the sampled receiver solution was measured by HPLC.

The results are shown in Table 2.

TABLE 2

|  | Ex. 1 | Ex. 2 | Comp. Ex. 1 | Comp. Ex. 2 | Comp. Ex. 3 | Comp. Ex. 4 |
|---|---|---|---|---|---|---|
| ① 12–24 h | 22.743 | 32.577 | 60.900 | 77.431 | 84.784 | 66.175 |
| ② 32–48 h | 26.263 | 27.418 | 32.595 | 26.619 | 30.891 | 25.010 |
| ②/① × 100 (%) | 115.5 | 84.2 | 53.5 | 34.4 | 36.4 | 37.8 |

Example 3

A gel cream was obtained in the usual manner according to a formulation containing 2% by mass of lidocaine hydrochloride, 0.02% by mass of dexamethasone acetate, 1% by mass of polyoxyethylene sorbitan monostearate, 5% by mass of liquid paraffin, 1% by mass of stearyl alcohol, 10% by mass of dipropylene glycol, 1% by mass of polyvinyl pyrrolidone K30, 0.5% by mass of carboxyvinyl polymer, 1% by mass of diisopropanolamine, and purified water to make a total of 100 g.

Example 4

A liquid preparation (pH =6.67) was obtained according to a formulation containing 1% by mass of lidocaine hydrochloride, 0.1% by mass of carboxyvinyl polymer, 1.0% by mass of polyvinyl pyrrolidone, 0.125% by mass of triethanolamine, 10% by mass of polyethylene glycol 400, 50% by mass of ethanol, and purified water to make a total of 100 ml.

Example 5

A gel cream was obtained according to a formulation containing 1.0% by mass of miconazole nitrate, 2.0% by mass of polyoxyethylene sorbitan monostearate, 5.0% by mass of middle chain fatty acid triglyceride (panasate), 1.0% by mass of stearyl alcohol, 1.0% by mass of cetanol, 1.5% by mass of polyvinyl pyrrolidone K90, 0.3% by mass of carboxyvinyl polymer, 0.35% by mass of diethanolamine, 1.0% by mass of sorbitan monostearate, and purified water to make a total of 100 g.

INDUSTRIAL APPLICABILITY

The present invention was able to provide a new technique for permitting a basic drug to be long acting. Thus, the preparation of the present invention is useful, for example, as a once-daily-administered preparation for external use capable of showing a long-lasting action even on a damaged skin.

What is claimed is:

1. A preparation for external use, containing a basic drug, polyvinyl pyrrolidone and a carboxyvinyl polymer and an amount of an amine based neutralizing agent which is required to neutralize the carboxyvinyl polymer and having a pH of 4 to 9.

2. The preparation for external use according to claim 1, whose dosage form is a liquid.

3. The preparation for external use according to claim 1, wherein the amount of the carboxyvinyl polymer added is 0.1 to 6 parts by mass per part by mass of the basic drug.

4. The preparation for external use according to claim 1, wherein the amount of the polyvinyl pyrrolidone added is 0.5 to 10 parts by mass per part by mass of the basic drug.

5. The preparation for external use according to claim 1, further containing polyethylene glycol.

6. The preparation for external use according to claim 5, wherein the amount of the polyethylene glycol added is 10 to 50% by mass based on the entire mass of the preparation.

7. The preparation for external use according to claim 1, further containing an alcohol.

8. The preparation for external use according to claim 7, wherein the alcohol is one or more alcohols selected from the group consisting of ethanol, isopropanol, isostearyl alcohol, propylene glycol, 1,3-butylene glycol and dipropylene glycol.

9. The preparation for external use according to claim 7, wherein the amount of the alcohol added is 10 to 70% by mass based on the entire mass of the preparation.

10. The preparation for external use according to claim 1, wherein the amine-based neutralizing agent is selected from the group consisting of triethanolamine, diethanolamine, triethylamine, diethylamine, isopropanolamine, diisopropanolamine, triisopropanolamine, di(2-ethylhexyl) amine, tetrahydroxypropylethylenedi amine, and monoethanolamine.

* * * * *